United States Patent [19] [11] 4,343,749
Siegemund et al. [45] Aug. 10, 1982

[54] PROCESS FOR THE PREPARATION OF MONOHYDROPERFLUOROALKANE-SULFONIC ACID HALIDES AND SOME SPECIFIC REPRESENTATIVES OF THIS CLASS OF COMPOUND

[75] Inventors: Günter Siegemund, Hofheim am Taunus; Werner Schwertfeger, Butzbach, both of Fed. Rep. of Germany

[73] Assignee: Hoechst Aktiengesellschaft, Frankfurt am Main, Fed. Rep. of Germany

[21] Appl. No.: 300,918

[22] Filed: Sep. 10, 1981

[30] Foreign Application Priority Data

Sep. 12, 1980 [DE] Fed. Rep. of Germany ....... 3034537

[51] Int. Cl.³ ............................................ C07C 143/70
[52] U.S. Cl. .............................. 260/543 F; 260/543 R
[58] Field of Search ......................... 260/543 F, 543 R

[56] References Cited

U.S. PATENT DOCUMENTS 2,950,317 8/1960 Brown et al. ................... 260/543 F
3,641,140 2/1972 Keberle ............................ 260/543 R
3,920,738 11/1975 Martin ............................. 260/543 F
4,005,138 1/1977 Plattner et al. ................. 260/543 F
4,060,549 11/1977 Schmidt et al. ................. 260/543 F

FOREIGN PATENT DOCUMENTS 1964988 7/1971 Fed. Rep. of Germany ... 260/543 R

Primary Examiner—Natalie Trousof
Assistant Examiner—Frederick W. Pepper
Attorney, Agent, or Firm—Curtis, Morris & Safford

[57] ABSTRACT

Monohydroperfluoroalkanesulfonic acid halides of the formula I

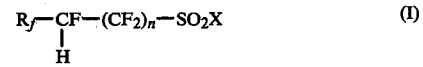

(I)

in which $R_f = F$ or perfluoroalkyl, $X = Cl$ or $F$ and $n = 1-7$, are prepared by reacting monohydroperfluoroalkanesulfonic acids of the formula II

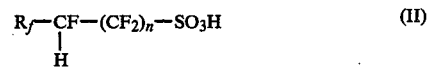

(II)

in which $R_f$ and n have the same meaning as in formula I, with pyrocatechol-phosphorus trichloride (→compounds I in which $X = Cl$) and, if desired, further reacting the products with alkali metal fluorides and/or alkali metal hydrogen fluorides (→compounds I in which $X = F$). With the exception of the compound in which $R_f = F$, $n = 1$ and $X = Cl$ ($= HCF_2-CF_2-SO_2Cl$), the compounds I are new.

The compounds I are chiefly intermediates in organic fluorine chemistry, in particular for the preparation of perfluorinated ion exchanger resins containing sulfonic acid groups.

5 Claims, No Drawings

PROCESS FOR THE PREPARATION OF MONOHYDROPERFLUOROALKANE-SULFONIC ACID HALIDES AND SOME SPECIFIC REPRESENTATIVES OF THIS CLASS OF COMPOUND

Monohydroperfluoroalkanesulfonic acids of the formula $$R_f\text{—CHF—}(CF_2)_n\text{—SO}_3H$$

in which n=1 and $R_f$=fluorine or perfluoroalkyl, are chiefly accessible by addition of sodium bisulfite onto perfluoroolefins [J. Org. Chem. 14, 747 (1949); and J. Am. Chem. Soc. 74, 4,595 (1953)]:

$$R_f\text{—CF=CF}_2 \xrightarrow[\text{2. H}^\oplus]{\text{1. NaHSO}_3} R_f\text{—CHF—CF}_2\text{—SO}_3H$$

or by hydrolysis of perfluorinated cyclic sulfones [J. Fluorine. Chem. 13, 251 (1979)]:

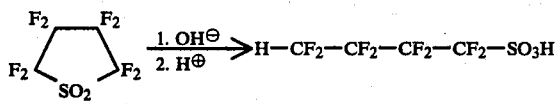

In one case, the sulfonic acid chloride also has already been formed from such a sulfonic acid with the aid of phosphorus pentachloride [J. Org. Chem. 14, 747 (1949)]:

$$H\text{—CF}_2\text{—CF}_2\text{—SO}_3H \xrightarrow[\text{—POCl}_3]{+\text{PCl}_5} H\text{—CF}_2\text{—CF}_2\text{—SO}_2Cl$$

Phosphorus oxychloride is formed as a by-product, and can be separated off from the sulfonic acid chloride only with difficulty. No yield is stated. The corresponding monohydroperfluoroalkanesulfonic acid fluoride has not yet been disclosed.

The object of this invention was thus to discover a simpler method of preparing monohydroperfluoroalkanesulfonic acid halides. The method should be generally applicable, and it should be possible to purify the products without a relatively great deal of effort.

It was possible to achieve this object according to the invention.

The invention relates to a process for the preparation of monohydroperfluoroalkanesulfonic acid halides of the formula I $$R_f\text{—}\underset{H}{\overset{|}{CF}}\text{—}(CF_2)_n\text{—SO}_2X \qquad (I)$$

in which $R_f$ denotes F or perfluoroalkyl with 1–10, preferably 1–8 and in particular 1–3, C atoms, X denotes Cl or F and n denotes a number from 1 to 7, which comprises (a) reacting monohydroperfluoroalkanesulfonic acids of the formula II $$R_f\text{—}\underset{H}{\overset{|}{CF}}\text{—}(CF_2)_n\text{—SO}_3H \qquad (II)$$

in which $R_f$ and n have the same meaning as in formula I, with pyrocatechol-phosphorus trichloride

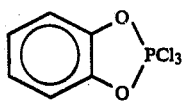

to give the monohydroperfluoroalkanesulfonic acid chlorides of the formula I in which X=Cl, and (b) if desired, then reacting these compounds further with an alkali metal fluoride and/or an alkali metal hydrogen fluoride, preferably in an aprotic, polar solvent, to give the monohydroperfluoroalkanesulfonic acid fluorides of the formula I in which X=F.

It was particularly surprising that stage (a) takes place—that the reaction of the monohydroperfluoroalkanesulfonic acids of the formula II with pyrocatechol-phosphorus trichloride to give the monohydroperfluoroalkanesulfonic acid chlorides of the formula I in which X=Cl takes place smoothly—in that pyracatechol-phosphorus trichloride, which is known for converting carboxylic acids into carboxylic acid chlorides [compare Chem. Ber. 96,1,387 (1963)], is also suitable here for converting the sulfonic acids II into the sulfonic acid chloride I (in which X=Cl). In fact, sulfonic acids cannot be converted into the sulfochlorides in an analogous manner, for example, by means of thionyl chloride, which is also known for converting carboxylic acids into their acid chlorides [J. Org. Chem. 14, 747 (1949)].

The monohydroperfluoroalkanesulfonic acids of the formula II employed as starting compounds for the process according to the invention can be obtained, for example, by the abovementioned known processes; that is to say from perfluoroolefins and sodium bisulfite in accordance with the method of J. Org. Chem. 14, 747 (1949) and J. Am. Chem. Soc. 75,4,595 (1953) and from perfluorinated cyclic sulfones in accordance with the method of J. Fluorine Chem. 13, 251 (1979).

In stage (a) of the process, the sulfonic acid II is thus in general reacted with the pyrocatechol-phosphorus trichloride in a molar ratio of about 1:1. An excess of pyrocatechol-phosphorus trichloride is not in itself necessary; however, an approximately 5 to 50% excess is preferred.

Stage (a) is in general carried out without a solvent; however, it can also be carried in an aprotic inert solvent. If the latter is done (carrying out the stage in an aprotic inert solvent), possible solvents are, for example: $CCl_4$, $CHCl_3$, diglyme or tetraglyme and the like.

The reaction temperature is usually between about 20° and about 180° C., but is preferably between about 60° and about 140° C.

The sequence in which the reactants are brought together is practically of no importance for carrying out stage (a) of the process according to the invention. Nevertheless, it is advantageous to ensure uniform thorough mixing of the batch by stirring well.

In a preferred procedure, the pyrocatechol-phosphorus trichloride is initially introduced into the reaction vessel and is heated to above its melting point. The sulfonic acid II is then added dropwise. When the evolution of gas has ended, the sulfonic acid chloride of the formula I (in which X=Cl) formed is advantageously separated off by distillation.

The sulfonic acid chlorides of the formula I in which X=F can then be prepared from the sulfonic acid chlorides of the formula I in which X=Cl by stage (b) of the process according to the invention. This preparation is carried out by means of an alkali metal fluoride and/or alkali metal hydrogen fluoride or a mixture of at least two of these fluorides, preferably in an aprotic polar solvent.

For this stage to take place, it is in principle unnecessary to employ more than about 1 mole of alkali metal fluoride and/or alkali metal hydrogen fluoride; however, an approximately 5 to 50% excess is preferred.

Whilst stage (a) can indeed be carried out in an aprotic inert solvent, but this is not preferred for this stage, the use of such a solvent is preferred in stage (b). Possible solvents are: nitriles, such as acetonitrile or butyronitrile, ethers, such as diethylene glycol dimethyl ether or tetraethylene glycol dimethyl ether, acid amides, such as dimethylformamide or dimethylacetamide, sulfoxides, such as dimethylsulfoxide, sulfolane and the like.

The reaction temperature in stage (b) is in general between about 0° and about 160° C., but preferably between about 40° and about 120° C.

As for stage (a) of the process, the sequence in which the reactants (and the solvent) are brought together is also practically of no importance for stage (b). In this case also, it is advantageous for the batch to be uniformly mixed thoroughly by stirring well.

A preferred procedure for stage (b) comprises initially introducing the alkali metal fluoride and/or alkali metal hydrogen fluoride into the particular aprotic polar solvent and then adding the sulfonic acid chloride I (in which X=Cl). The mixture is then heated. The sulfofluoride I (in which X=F) formed thereby distills off.

Apart from the compound $HCF_2-CF_2-SO_2Cl$ (=compound of the formula I in which $R_f$=F, n=1 and X=Cl), the monohydroperfluoroalkanesulfonic acid halides of the formula I prepared according to the invention are new.

The monohydroperfluoroalkanesulfonic acid halides I prepared according to the invention are particularly valuable intermediates in organic fluorine chemistry. They are particularly advantageously first converted into fluorosulfatoperfluorosulfonic acid halides by the process of Patent Application Ser. No. 300,916 filed on the same day, by electrolysis in an electrolyte consisting of fluorosulfonic acid and an alkali metal fluorosulfonate, using anodes of glassy carbon and cathodes of a customary material which is stable under the electrolysis conditions, and from these products the corresponding perfluorocarbonylsulfonic acid fluorides are obtained in the presence of alkali metal fluorides, as catalysts:

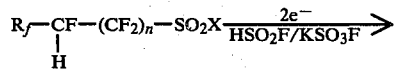

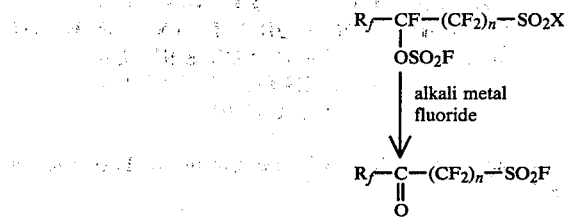

The resulting perfluorocarbonylsulfonic acid fluorides can then in turn be converted into perfluorovinyl compounds containing sulfonic acid fluoride groups in a known manner, for example with hexafluoropropene epoxide

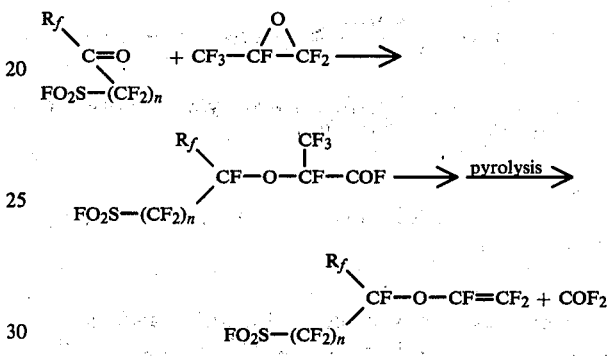

and homopolymerization or copolymerization (for example with tetrafluoroethylene) of these perfluorovinyl compounds, followed by hydrolysis (of the sulfofluoride groups), leads to valuable perfluorinated ion exchangers.

Since the further processing outlined above for the monohydroperfluoroalkanesulfonic acid halides I proceeds better with the fluorides (X=F) than with the chlorides (X=Cl), it is advantageous to use the fluorides as the starting material.

The invention will now be illustrated in more detail by the examples which follow.

EXAMPLE 1

(a) 2-H-tetrafluoroethanesulfonic acid chloride

817 g (3.3 moles) of pyrocatechol-phosphorus trichloride are initially introduced into a dry flask with a magnetic stirrer, reflux condenser, dropping funnel and bubble counter, and are warmed to about 80° C. 585 g (3.22 moles) of 2-H-tetrafluoroethanesulfonic acid are then added dropwise. The reaction starts immediately and HCl gas escapes. When the evolution of gas has ended, the batch is distilled. 430 g (67%) of 2-H-tetrafluoroethanesulfonic acid chloride are obtained with a boiling point of 90°–92° C. (758 mm).

(b) 2-H-tetrafluoroethanesulfonic acid fluoride

400 ml of acetonitrile, 145 g (2.5 moles) of potassium fluoride and 50 g (0.64 mole) of potassium hydrogen fluoride are initially introduced into a dry flask with a stirrer, thermometer, dropping funnel, Vigreux column and column head. 430 g (2.15 moles) of 2H-tetrafluoroethanesulfonic acid chloride are added dropwise, with good stirring. The batch is heated to an internal temperature of 70°–80° C. The sulfonic acid fluoride formed is distilled off from the mixture. Fractionation of the crude product over a packed column gives 358 g of (91%) of 2-H-tetrafluoroethanesulfonic acid fluoride with a boiling point of 46° C. (755 mm).

Analysis: Calculated: C, 13.05; H, 0.55; F, 51.60; S, 17.42. Found: C, 13.0; H, 0.5; F, 51.3; S, 17.4.

$^1$H-NMR (CDCl$_3$): 6.20 (ttd, J=52, 4.5 and ~1.5 Hz)

$^{19}$F-NMR (CDCl$_3$)*:+44.3 (m, 1F, —SO$_2$F), −114.71 (m, 2F, —CF$_2$—S), −139.52 (dq, J=52 and 6.5 Hz, 2F, —CF$_2$H)

*CFCl$_3$ serves as the internal standard in all the $^{19}$F-NMR spectra.

IR (gas spectrum): 6.82μ (SO)

EXAMPLE 2

(a) 2-H-hexafluoropropanesulfonic acid chloride
CF$_3$—CHF—CF$_2$—SO$_2$Cl 470 g (1.92 moles) of pyrocatechol-phosphorus trichloride and 400 g (1.72 moles) of 2-H-hexafluoropropanesulfonic acid are reacted in accordance with the instructions in Example 1. 377 g (87%) of 2-H-hexafluoropropanesulfonic acid chloride with a boiling point of 104° C. (760 mm) are obtained.

Analysis: Calculated: C, 14,38; H, 0.40; F, 45.50; Cl, 14.15; S, 12.80. Found: C, 14.6; H, 0.5; F, 45.1; Cl, 15.2; S, 13.0.

$^1$H-NMR (CDCl$_3$): 5.40 (dm, $^2$J$_{H,F}$=43 Hz)

$^{19}$F-NMR (CDCl$_3$)*: −73.95 (m, 3F, CF$_3$), −101.6 (δm, J$_{gem}$=230 Hz, 1F, CF$_2$), −111.7 (δm, J$_{gem}$=230 Hz, 1F, CF$_2$), −210.46 (m, 1F, CF)

IR (gas spectrum): 7.03μ (SO)

(b) 2-H-hexafluoropropanesulfonic acid fluoride
CF$_3$—CHF—CF$_2$—SO$_2$F 145 g (2.5 moles) of potassium fluoride, 16 g (0.2 mole) of potassium hydrogen fluoride and 546 g of (2.18 moles) of 2-H-hexafluoropropanesulfonic acid chloride in 800 ml of butyronitrile are reacted in accordance with the instructions in Example 1b. Fractionation over a packed column gives 312.5 g (61%) of 2-H-hexafluoropropanesulfonic acid fluoride with a boiling point of 63.5° C. (760 mm).

Analysis: Calculated: C, 15.39; H, 0.43; F, 56.81; S, 13.70. Found: C, 15.55; H, 0.45; F, 56.65; S, 13.85.

$^1$H-NMR (CDCl$_3$): 5.40 (d m, J=43 Hz)

$^{19}$F-NMR (CDCl$_3$)*: +41.87 (m, 1F, SO$_2$F), −74.5 (m, 3F, CF$_3$), −106.6 (δm, J=256 Hz, 1F, —CF$_2$—S), −113.8 (δm, J=256 Hz, 1F, —CF$_2$—S—), −211.6 (δm, J=43 Hz, 1F, —CHF)

IR (gas spectrum): 6.78μ (SO)

We claim:

1. A process for the preparation of a monohydroperfluoroalkanesulfonic acid halide of the formula I

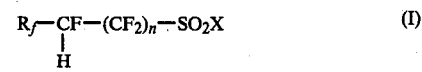

in which R$_f$ denotes F or perfluoroalkyl with 1–10, preferably 1–8 and in particular 1–3, C atoms, X denotes Cl or F and n denotes a number from 1 to 7, which comprises (a) reacting a monohydroperfluoroalkanesulfonic acid of the formula II

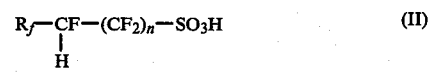

in which R$_f$ and n have the same meaning as in formula I, with pyrocatechol-phosphorus trichloride to give the monohydroperfluoroalkanesulfonic acid chloride of the formula I in which X=Cl, and (b) if desired, then reacting this compound further with at least one alkali metal fluoride and/or an alkali metal hydrogen fluoride, preferably in an aprotic, polar solvent, to give the monohydroperfluoroalkanesulfonic acid fluoride of the formula I in which X=F.

2. A process as claimed in claim 1, wherein about 1 to 1.5 moles of pyrocatechol-phosphorus trichloride are employed, in stage (a), per mole of monohydroperfluoroalkanesulfonic acid of the formula II.

3. A process as claimed in claim 1 or 2, wherein stage (a) is carried out at temperatures between about 20° and 180° C., preferably between about 60° and 140° C.

4. A process as claimed in any one of claims 1 to 3, wherein about 1 to 1.5 moles of alkali metal fluoride and/or alkali metal hydrogen fluoride are employed, in stage (b), per mole of monohydroperfluoroalkanesulfonic acid chloride of the formula I in which X=Cl.

5. A process as claimed in any of claims 1 to 4, wherein stage (b) is carried out at temperatures between about 0° and 160° C., preferably about 40° and 120° C.

* * * * *